United States Patent
Haga

[11] Patent Number: 5,497,234
[45] Date of Patent: Mar. 5, 1996

[54] INSPECTION APPARATUS

[76] Inventor: Kazumi Haga, c/o New Creation 2-1 Koshino, Hachioji-shi, Tokyo-to, Japan

[21] Appl. No.: 208,311

[22] Filed: Mar. 10, 1994

[30] Foreign Application Priority Data

Apr. 30, 1993 [JP] Japan ................... 5-127883

[51] Int. Cl.⁶ ................................. G01N 21/00
[52] U.S. Cl. .......................... 356/371; 356/237
[58] Field of Search ................... 356/371, 237, 356/445, 446

[56] References Cited

U.S. PATENT DOCUMENTS

| | | |
|---|---|---|
| 3,782,836 | 1/1974 | Fey et al. . |
| 3,815,998 | 6/1974 | Tietze ................... 356/237 |
| 3,892,492 | 7/1975 | Eichenberger .......... 356/446 |
| 4,215,939 | 8/1980 | Miller et al. ............ 356/237 |
| 4,285,597 | 8/1981 | Lamprecht et al. ..... 356/446 |
| 4,421,410 | 12/1983 | Karasaki . |
| 4,643,540 | 2/1987 | Kawasaki et al. . |
| 4,682,040 | 7/1987 | Hohki et al. ............ 356/446 |
| 4,871,257 | 10/1989 | Suzuki et al. ........... 356/237 |
| 5,039,225 | 8/1991 | Uekusa ................... 356/446 |
| 5,239,171 | 2/1992 | Takabayashi et al. . |
| 5,286,943 | 2/1994 | Torigoe . |
| 5,305,054 | 4/1994 | Suzuki et al. . |

FOREIGN PATENT DOCUMENTS 590366 4/1993 Japan .

*Primary Examiner*—Richard A. Rosenberger
*Attorney, Agent, or Firm*—Evenson, McKeown, Edwards & Lenahan

[57] ABSTRACT

An inspection apparatus has a light source for irradiating lights to a sample. An optical element comprising of an achromatic lens converges the lights transmitted through or reflected by the sample to thereby form an image behind the back focal plane. An aperture stop is arranged at or near the back focal plane tot eliminating the lights scattered or refracted by the sample. The image is observed with a camera tube arranged behind the back focal plane.

5 Claims, 5 Drawing Sheets

INSPECTION APPARATUS

BACKGROUND OF THE INVENTION

1. Field of the Invention

The present invention relates generally to an inspection apparatus. and more particularly to an inspection apparatus suited for detecting marks formed on a sample surface.

2. Description of Background Art

In usual, ID numbers (marks) are formed on a surface of each semiconductor wafer identifying for example a type of product and a name of customer in order to manage the manufacturing process of semiconductor using the marks. The ID numbers are conventionally read with the naked eye of an operator.

The ID numbers are formed on the semiconductor wafer near the orientation flat thereof. A portion near the orientation flat is a region in which a pattern of circuits or wiring is not usually formed and thus no film of insulation or conductor is coated. Accordingly, it is usually possible to read the ID numbers by the naked eye. However, in a occasional case in which some pattern would be formed near the orientation flat, or in a case in which the ID numbers would be coated by a resist film for a pattern formation due to a position shift of the pattern during the pattern forming step and other reasons, substantial time is required for reading the ID numbers since lights scattered by the pattern and the resist surface detract the visibility of the ID numbers.

On the other hand, although there is another inspection apparatus in which the ID numbers Are read by using an optical system, it is very difficult to read the ID numbers if they are coated by any film coating.

SUMMARY OF THE INVENTION

It is therefore an object of the present invention to provide an inspection apparatus which can easily read ID numbers formed on a sample surface although when the ID numbers are coated by any film coating.

For achieving the object, according to the present invention, there is provided an inspection apparatus for observing a sample, comprising:

light irradiating means for irradiating lights to a sample;

an optical element comprising of an achromatic lens having a back focal plane for converging the lights transmitted through or reflected by the sample to form an image behind the back focal plane;

an aperture stop arranged at or near the back focal plane for eliminating the lights scattered or retracted by the sample; and observing means arranged behind the back focal plane for observing the image.

According to a preferable embodiment of the present invention, there is provided an inspection apparatus for observing a sample, further comprising second light irradiating means for irradiating lights to the sample at an incident angle larger than that of the light irradiating means.

Further according to the present invention, there is provided an inspection apparatus for observing a sample, comprising:

a plurality of light irradiating means for irradiating lights to a sample in different incident directions from each other;

an optical element comprising of an achromatic lens having a back focal plane for converging the lights transmitted through or reflected by the sample to form an image behind the back focal plane;

an aperture stop arranged at or near the back focal plane for eliminating the lights scattered or refracted by the sample; and observing means arranged behind the back focal plane for observing the image.

According to these inspection apparatus of the present invention, since the observation can be carried out with setting the focus on the sample, and since almost all the scattered or refracted lights can be cut off by the aperture stop, the visibility of the obtained reflected or transmitted image is remarkably improved. In addition, since a light/dark pattern exhibiting a condition of the whole surface of or the inside of the sample is formed behind a portion screened by the aperture stop, it is possible to observe at once the condition of the whole surface of or the inside of the sample and also to easily read the marks coated by the film coating. Furthermore, the use of the achromatic lens can eliminate the chromatic abberation and thus further improves the visibility of the reflected image.

DESCRIPTION OF THE PREFERRED EMBODIMENTS

Preferred embodiments of an inspection apparatus of the present invention will be hereinafter described with reference to the accompanying drawings.

First Embodiment

Figure 1:
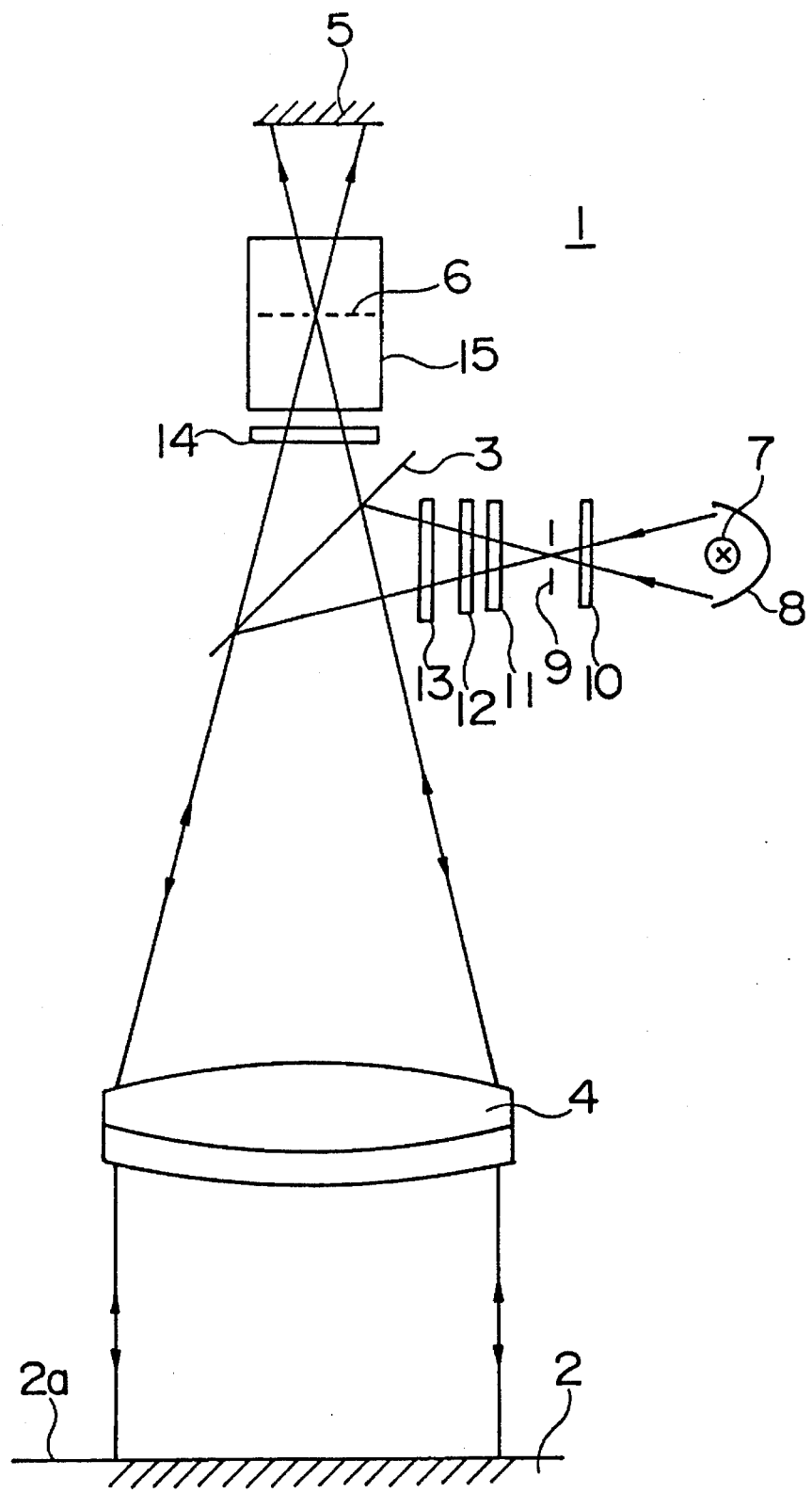
FIG. 1 is a schematic view of a first embodiment of an optical system of the inspection apparatus of the present invention.

FIG. 1 shows an optical system 1 of an inspection apparatus of a first embodiment of the present invention. First of all, the whole structure of the optical system 1 will be generally explained. The optical system is structured such that it irradiates parallel lights perpendicularly to a surface 2a of a plate-shaped sample 2 (hereinafter reffered to "sample surface 2a") through a beam splitter (or a half mirror) 3 and a collimator lens 4, then converges reflected lights from the sample surface 2a at a back focal plane, and finally observes a reflected image by using a camera tube 5 behind the back focal plane. During the observation, the lights scattered or diffused by the sample surface 2a are adapted to be cut off by an aperture stop 6 arranged at the back focal plane.

Then the optical system 1 will be described more in detail.

In this optical system 1, a xenon lamp or a halogen lamp may be used as a light source 7, however, this is not definitive. The type of the lamp to be used as the light source 7 is determined in accordance with the nature of the inspection object (i.e. the sample 2). For example, in case of inspecting an object having a relatively high reflectivity such as a semiconductor wafer, either the halogen lamp or the xenon lamp may be used, on the other hand, in case of inspecting an object having a relatively low reflectivity such as a glass substrate, it is preferable to use the xenon lamp having a higher luminance. Accordingly, it is preferable to make the light source 7 exchangeable in accordance with the nature of the object to be inspected.

An elliptical reflector 8 is combined with the light source 7. The light source 7 is positioned on one focal point of the elliptical reflector 8 and a pinhole 9 is positioned on the other focal point. Due to the nature of the ellipse, the lights reflected by the elliptical reflector 8 are converged at a position of the pinhole 9 and this creates the same condition as if a point light source would be in the position of the pinhole 9. The elliptical reflector 8 can be replaced with a parabolic reflector. In this case, since lights reflected by the parabolic reflector travel in parallel with its optical axis, another collimator lens is arranged so that it converges the parallel lights at the pinhole 9.

A heat wave absorbing filter 10 is arranged between the light source 7 and the pinhole 9, and also a wavelength selecting filter 11, a diffuser user 12 and a polarizing plate (polarizer) 13 are arranged between the pinhole 9 and the beam splitter 3. The heat wave absorbing filter 10 is used for cutting oil the infrared radiation in order to protect the optical system 1 from the heat wave. The wavelength selecting filter 11 is used for limiting the wavelength of the light to be irradiated to the sample surface 2a. The wavelength selecting filter 11 is detachable and can be used in accordance with the nature of the film coating on the sample surface 2a and the surface condition of the sample 2. For example, when the sample 2 is a semiconductor wafer provided with a film coating and specific wavelength band of lights has a bad influence (e.g. flaking etc.) on the film coating, the corresponding specific wavelength band should be cut off by the wavelength selecting filter 11. Also, since the wavelength selecting filter 11 has a function controlling sensitivity of the optical system 1, the filter 11 should be selected so that it can transmit and irradiate lights having short wavelength band on the sample surface 2a when the peak-to-valley of irregularity of the sample surface 2a is small. The diffuser 12 is also detachable and is used in case of rich in light composition of regular reflection such as when the sample surface 2a is a mirror surface as well as no film coating is formed thereon. For example, the diffuser 12 can be made of ground glass or opal glass. The polarizing plate 13 is used for transmitting a light wave having a specified plane of vibration and is able to change the vibration direction in which the lights can transmit therethrough by rotating the polarizing plate 13.

The collimator lens 4 arranged between the beam splitter 3 and the sample surface 2a is used for converting the lights passed through the pinhole 9 into parellel lights as well as for converge the lights reflected by the sample surface 2a. The collimator lens 4 is positioned so that the pinhole 9 is arranged at a front focal plane of the collimator lens 4. For example an achromatic lens (e.g. an achromatic lens of specific wavelength) or an apochromat lens may be used as the collimator lens 4 for eliminating chromatic aberration.

The beam splitter 3, a polarizing plate (analyzer) 14 and a camera lens (imagery system) 15 are arranged between the collimator lens 4 and the camera tube 5. The beam splitter 3 is used for deflecting the lights from the light source 7 downward. The polarizing plate 14, similarly to the polarizing plate 13, allows transmission of a light wave having a specified plane of vibration and also has a function of reducing glittering reflected lights. The polarizing plate 14 is also detachable. The camera lens 15 is incorporated with an aperture stop 6 and is movable both in vertical and horizontal planes.

An iris stop is used as the aperture stop 6 and is adapted to continuously change the diameter of the concentric opening thereof by moving its adjuster. With the change of the diameter of the opening, it is possible to obtain a reflected image suitable for each type of inspections (e.g. inspections of dimple, waviness and marks on the sample surface ).

According to the inspection apparatus of FIG. 1, the lights emitted from the light source 7 are reflected by the elliptical reflector 8 and then are converged at the pinhole 9 to form the point light source. The lights from the point light source are irradiated to the sample surface 2a through the wavelength selecting filter 11, the diffuser 12, the polarizing plate 13, the beam splitter 3 and the collimator lens 4.

Then, the lights reflected by the sample surface 2a are led to the camera tube 5 through the collimator lens 4, the beam splitter 3, the polarizing plate 14 and the aperture stop 6 arranged within the camera lens 15.

Following effects are obtained by the inspection apparatus having the optical system 1 of the present invention.

It is possible to improve the visibility of the reflected image and thus to easily read marks even though they are coated by a film coating, since the inspection apparatus of the present invention is able to observe the sample surface 2a with focusing thereon and is also able to eliminate almost all the scattered lights with the use of the aperture stop 6. In addition, it is possible to observe the whole surface condition of the sample 2 at once, since the whole condition of the sample surface is formed as a light/dark pattern behind the screened portion of the aperture stop 6.

Furthermore, it is possible to obtain a clear image without any chromatic aberration due to the use of the achromatic lens as the collimator lens 4.

Second Embodiment

Figure 2:
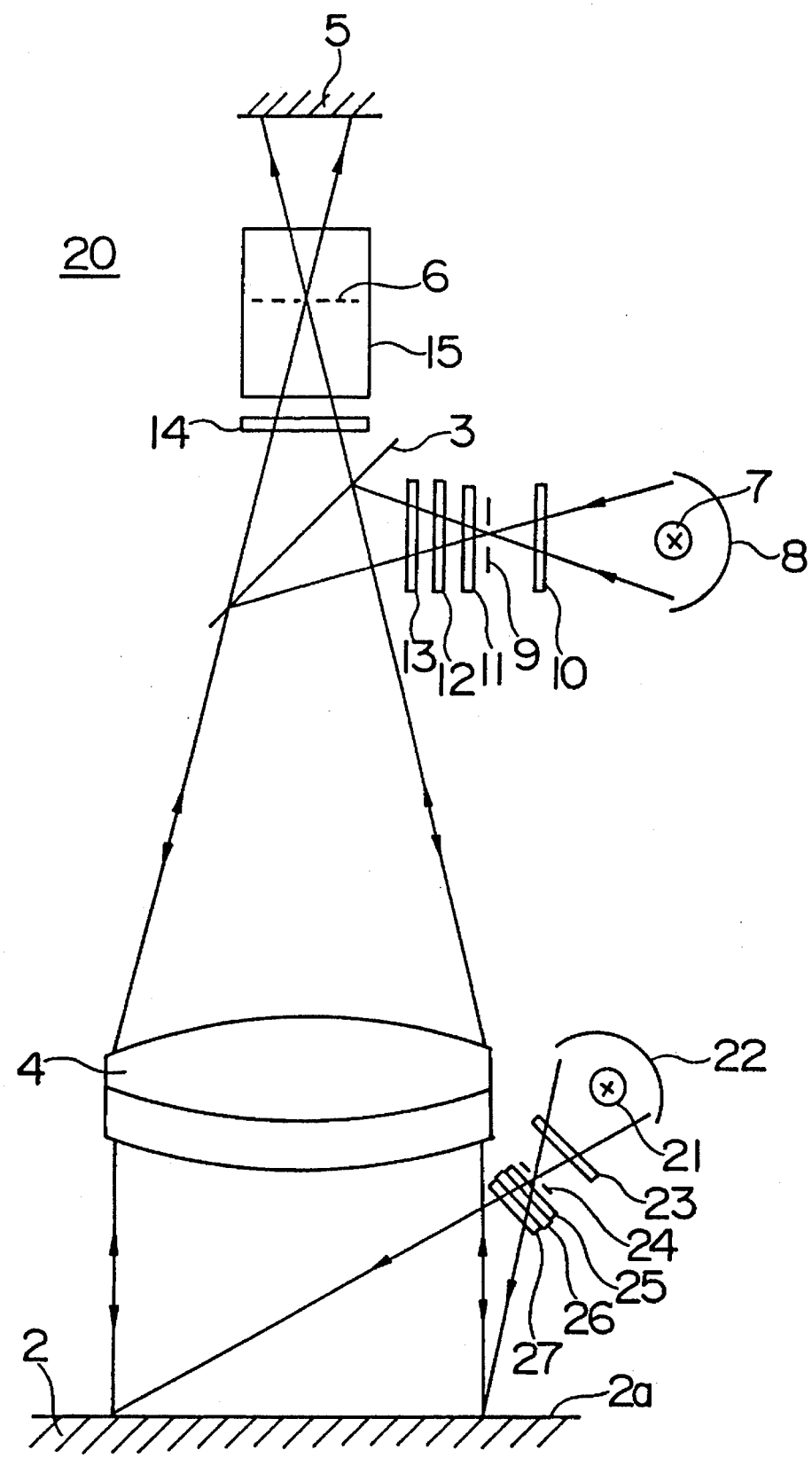
FIG. 2 is a schematic view a second embodiment of an optical system of the inspection apparatus of the present invention.

FIG. 2 shows an optical system 20 of a second embodiment. The optical system 20 is different from the optical system 1 of the first embodiment in that it has another light source 21 in addition to the light source 7. A halogen lamp or a xenon lamp may be used as the light source 21. Diffused lights from the light source 21 are irradiated to the sample surface 2a at an incident angle of 45° through a reflector 22, a heat wave absorbing filter 23, a pinhole 24, a wavelength selecting filter 25, a diffuser 26 and a polarizing plate 27. The wavelength selecting filter 25, the diffuser 26 and the polarizing plate 27 are detachable. The optical system on the side of the light source 21 is movable so as to enable the change of the incident angle or direction. The other structure is the same as that of the optical system 1 of the first embodiment and therefore the same reference numerals are also used in FIG. 2 for denoting the same components of FIG. 1 and explanations thereof are omitted.

According to the optical system 20 of the second embodiment, it is possible to increase the contrast of the reflected image, since the sample surface 2a is irradiated not only by the lights from a perpendicular direction but by the lights from an inclined direction.

Third Embodiment

Figure 3:
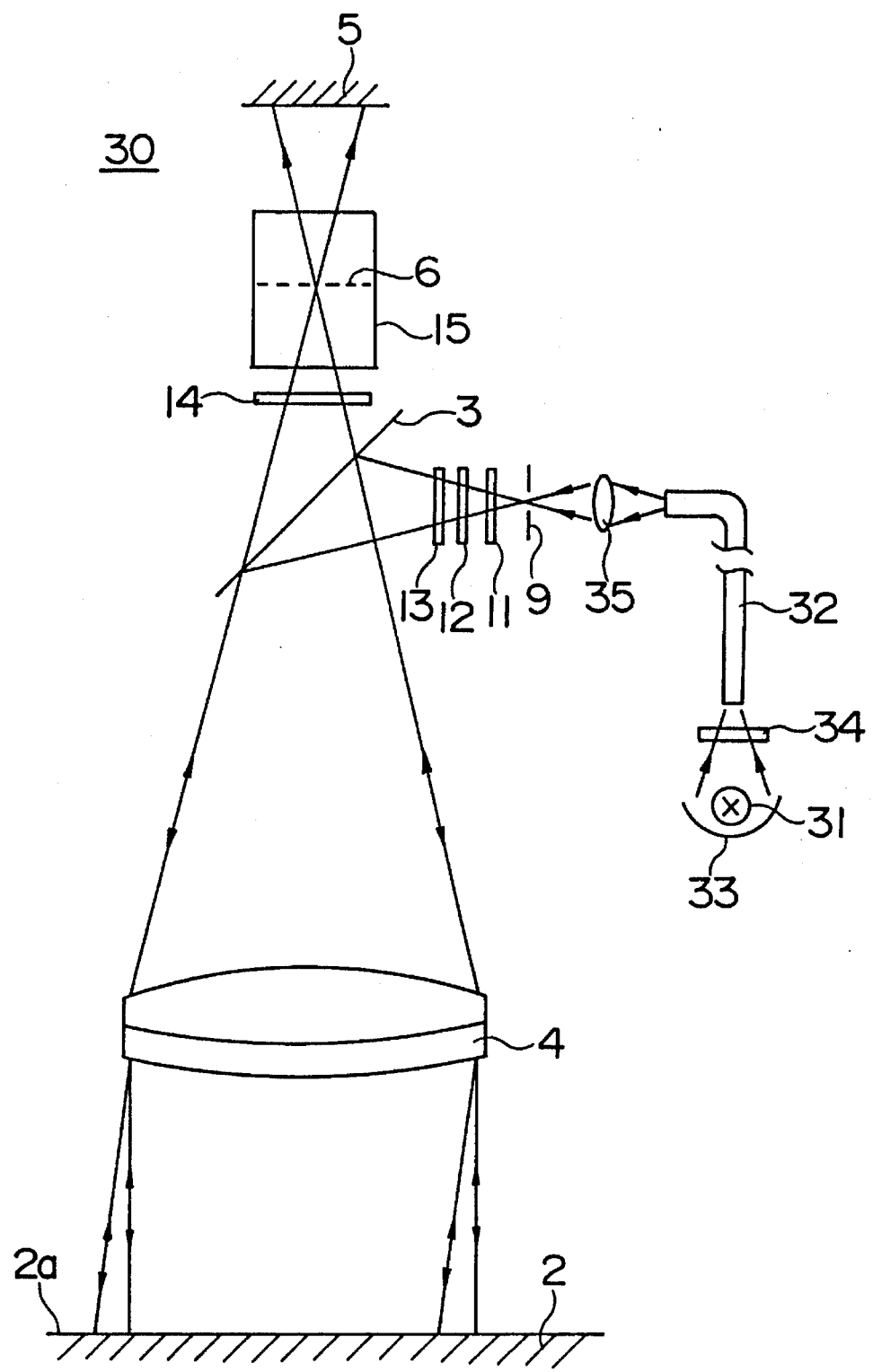
FIG. 3 is a schematic view of a third embodiment of an optical system of the inspection apparatus of the present invention.
Figure 4:
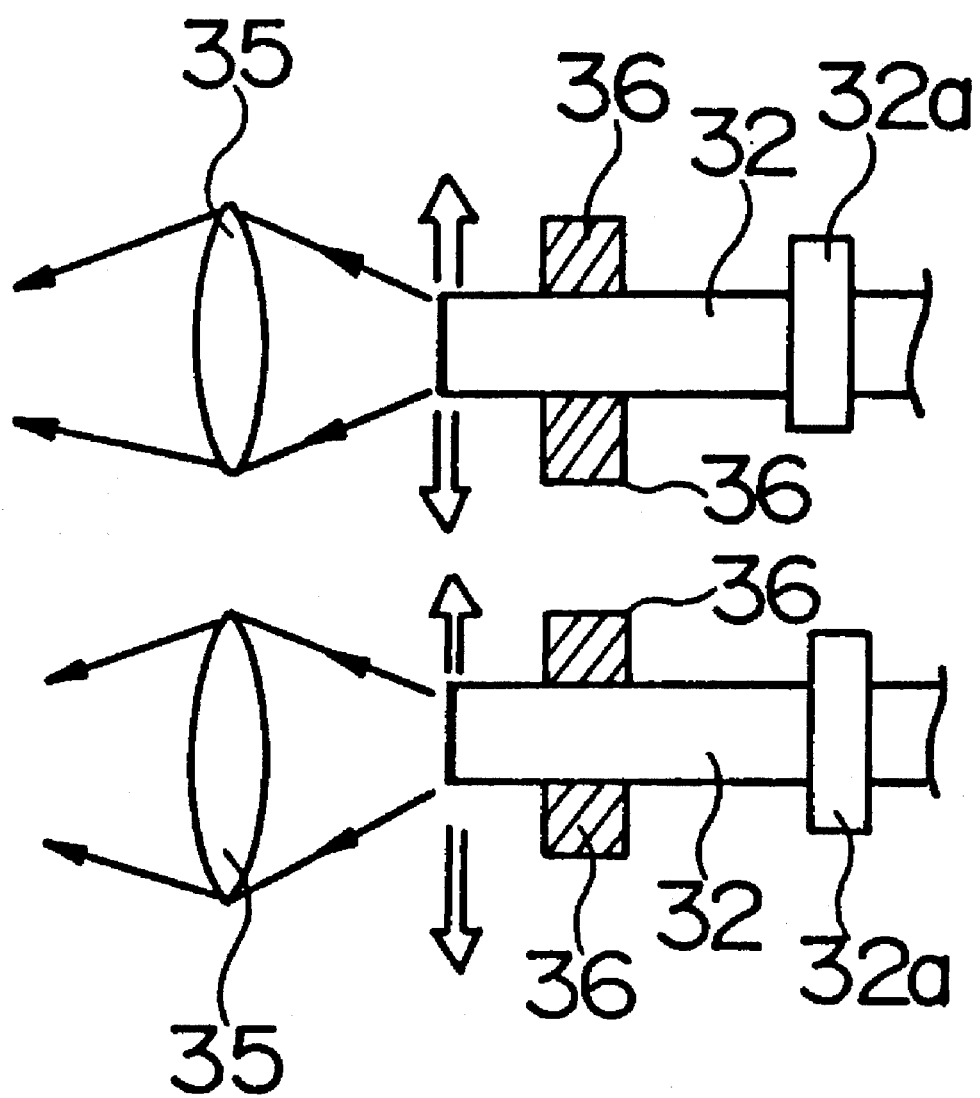
FIG. 4 is a plan view of a structure near a light-guide fiber of the third embodiment.

FIG. 3 shows an optical system 30 of a third embodiment. The optical system 30 is different from the optical system 1 of the first embodiment in its parallel light irradiating means. The light irradiating means of the third embodiment is constructed so as to irradiate lights from one or two light source 31 to the sample surface 2a through two light-guide fibers 32 and 32 as shown in FIG. 4. For example, in case of using one light source 31, the lights from the light source 31 are led to the two light-guide fibers 32 and 32 through a reflector 33 and a heat wave absorbing filter 34 and then the lights emitted from the two light-guide fibers 32 and 32 are irradiated to the sample surface 2a in two different directions through condenser lenses 35, the pinhole 9, the wavelength selecting filter 11, the diffuser 12, the polarizing plate 13, the beam splitter 3 and collimator lens 4. Each tip end of the two light-guide fibers 32 and 32 can be swung by the action of piezoelectric elements 36 by about 5° respectively in right and left-hand directions about each of their fulcrums 32a and 32a. Accordingly, each of the light-guide fibers 32 and 32 can be moved to its desirable position at which the clearest image can be obtained. The other structure is the same as that of the optical system 1 of the first embodiment and therefore the same reference numerals are also used in FIG. 3 for denoting the same components of FIG. 1 and explanations thereof are omitted.

Similar effect to that of the second embodiment can be obtained by the third embodiment. In addition, since the swing motion of the light-guide fibers 32 and 32 is made by the piezoelectric elements 36, the change of the light irradiating direction can be very easily carried out.

Fourth Embodiment

Figure 5:
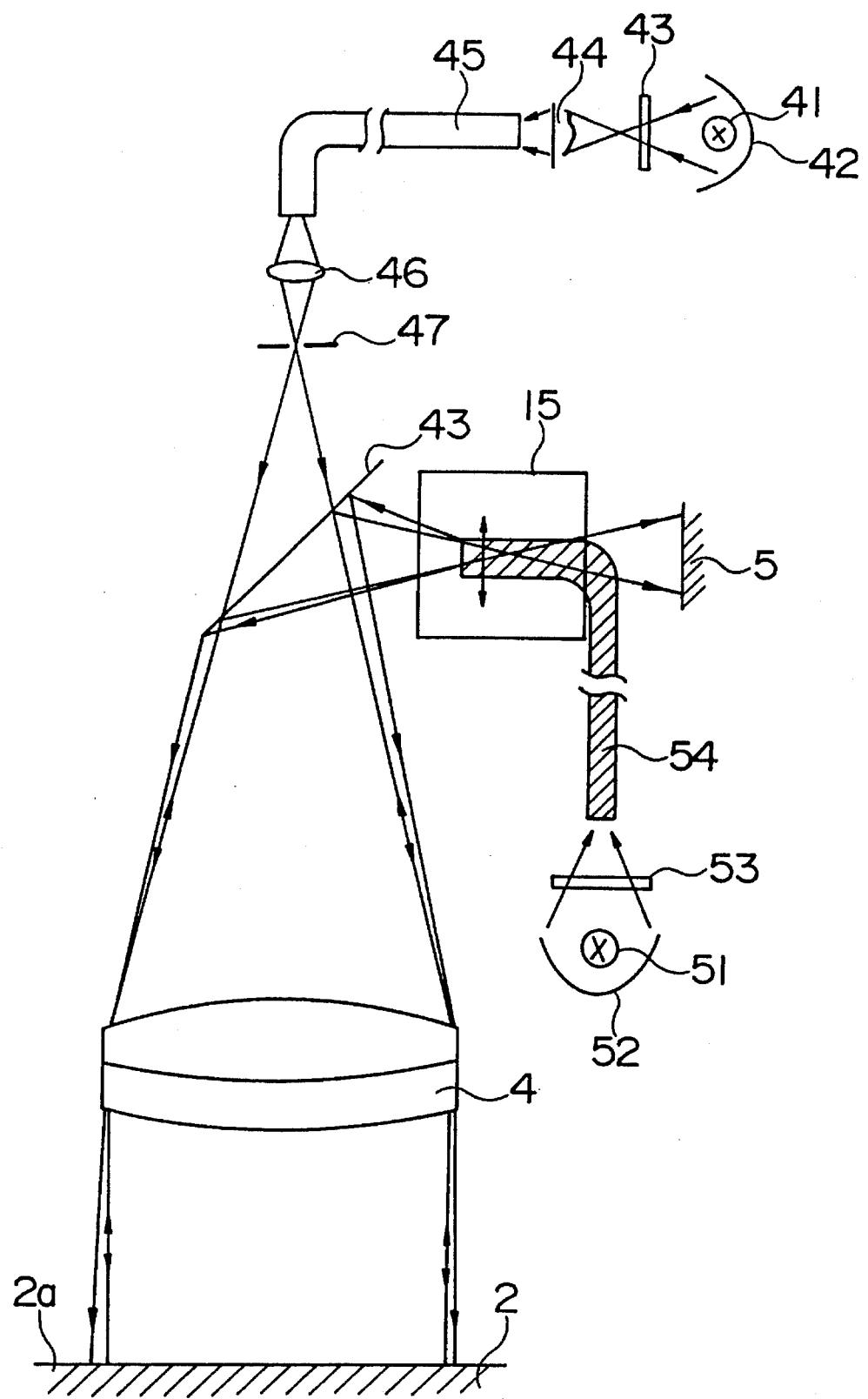
FIG. 5 is a schematic view of a fourth embodiment of an optical system of the inspection apparatus of the present invention.

FIG. 5 shows an optical system 40 of a fourth embodiment. In this optical system 40, lights from a light source 41 are irradiated to the sample surface 2a through a reflector 42, a heat wave absorbing filter 43, a condenser lens 44, a light-guide fiber 45, a condenser lens 46, a pinhole 47, the beam splitter 3 and the collimator lens 4 as well as lights from a light source 51 are also irradiated to the sample surface 2a through a reflector 52, a heat wave absorbing filter 53, a liquid light-guide fiber 54, the beam splitter 3 and the collimator lens 4. The observation of the sample surface 2a is carried out by the camera tube 5 through the camera lens (imagery system) 15. The liquid light-guide fiber 54 is mounted on the side of the camera lens 15 and each tip end of the liquid light-guide fiber 54 can be swung by about 5° respectively in a vertical direction. An aperture stop (not shown) is incorporated in the camera lens 15.

Similar effect to that of the second embodiment can be obtained by the fourth embodiment.

While the present invention has been described above with reference to several embodiments of the present invention, it should be understood that the present invention is not limited to the illustrated embodiments and that those skilled in the art will be able to make various modifications without departing from the scope of the present invention.

For example, although it is described in the illustrated embodiments to use the camera tube 5 for observing the reflected image of the sample surface 2a, it is possible to adopt an optical system for carrying out the observation by using a CCD, a conventional camera or the naked eye.

In addition, although it is described the case for inspecting a plate-shaped sample 2 with reference to the illustrated embodiments, an inspection of a cylindrical surface and a spherical surface can be carried out by irradiating lights perpendicularly to the surface with the use of a cylindrical lens for inspecting the cylindrical surface and of a plano-convex lens for inspecting the spherical surface. In a certain case, it is possible to use the cylindrical lens even for the inspection of the plate-shaped sample 2 by exaggerating the irregularity condition in a specified direction.

Furthermore, although it is described to use an iris stop as the aperture stop 6 with reference to the illustrated embodiments, it is possible to provide an aperture stop having a fixed circular aperture formed therein and to enable the aperture stop to move along the optical axis.

In addition, although it is described to position the aperture stop 6 at the back focal plane with reference to the illustrated embodiments, it may be set at any position near the back focal plane.

Furthermore, although it is described to observe the reflected image of the sample surface 2a with reference to the illustrated embodiments, it is possible to form the structure for observing a transmitted image of tha sample in order to observe the inside condition of the sample if the sample is transmissible.

What is claimed is:

1. An apparatus for inspecting the surface condition of an object, comprising:

(A) first light irradiating means for irradiating said object;

(B) an optical element comprising an achromatic lens having a back focal plane for converging the light reflected by the surface of the object at the back focal plane to form an image behind the back focal plane;

(C) an aperture stop arranged at or near the back focal plane for cutting off a scattered component of the reflected light;

(D) observing means arranged behind the back focal plane for observing the image; and (E) second light irradiating means for irradiating the object in a different incident direction from said first light irradiating means, said second light irradiating means being movable so as to change its incident direction relative to the object.

2. An apparatus for inspecting the surface conditions of an object according to claim 1, further comprising at least one light-guide fiber disposed in the path of the light emitted by said first irradiating means.

3. An apparatus for inspecting the surface condition of an object according to claim 1, wherein said incident direction is within a range which includes 45°.

4. An apparatus for inspecting the surface condition of an object according to claim 1, wherein said aperture stop is an iris diaphragm.

5. An apparatus for inspecting the surface condition of an object, comprising:

(A) a plurality of light irradiating means for irradiating said object in different incident directions from each other, at least one of said plurality of light irradiating means being movable so as to change its incident direction relative to the object;

(B) an optical element comprising an achromatic lens having a back focal plane for converging the light reflected by the surface of the object at the back focal plane to form an image behind the back focal plane;

(C) an aperture stop arranged at or near the back focal plane for cutting off a scattered component of the reflected light; and (D) observing means arranged behind the back focal plane for observing the image.

* * * * *